(12) United States Patent
Bogaert (10) Patent No.: US 8,974,526 B2
(45) Date of Patent: *Mar. 10, 2015

(54) MULTIZONAL LENS WITH EXTENDED DEPTH OF FOCUS

(75) Inventor: Theophilus Bogaert, Groningen (NL)

(73) Assignee: AMO Groningen B.V., Groningen (NL)

( * ) Notice: Subject to any disclaimer, the term of this patent is extended or adjusted under 35 U.S.C. 154(b) by 895 days.

This patent is subject to a terminal disclaimer.

(21) Appl. No.: 12/398,933

(22) Filed: Mar. 5, 2009

(65) Prior Publication Data

US 2010/0057202 A1  Mar. 4, 2010

Related U.S. Application Data

(63) Continuation-in-part of application No. 11/845,682, filed on Aug. 27, 2007.

(51) Int. Cl.
*A61F 2/16* (2006.01)
*G02C 7/04* (2006.01)
*A61F 2/14* (2006.01)

(52) U.S. Cl.
CPC ............. *A61F 2/1618* (2013.01); *A61F 2/1602* (2013.01); *G02C 2202/02* (2013.01); *G02C 7/04* (2013.01); *G02C 7/041* (2013.01); *A61F 2/14* (2013.01)
USPC ........................................ 623/6.27; 623/6.28

(58) Field of Classification Search
USPC .............. 623/6.27, 6.28, 6.3, 6.31, 6.32, 6.34
See application file for complete search history.

(56) References Cited

U.S. PATENT DOCUMENTS

| 2,077,092 | A |   | 4/1937  | Broder |
|-----------|---|---|---------|--------|
| 3,305,294 | A |   | 2/1967  | Alvarez |
| 3,367,734 | A | * | 2/1968  | Bystricky et al. ............. 359/686 |
| 3,735,685 | A |   | 5/1973  | Plummer |
| 4,010,496 | A |   | 3/1977  | Neefe |
| 4,077,071 | A |   | 3/1978  | Freeman |
| 4,093,361 | A |   | 6/1978  | Erickson et al. |
| 4,134,160 | A |   | 1/1979  | Bayers |
| 4,162,122 | A |   | 7/1979  | Cohen |
| 4,174,543 | A |   | 11/1979 | Kelman |
| 4,210,391 | A |   | 7/1980  | Cohen |
| 4,249,272 | A |   | 2/1981  | Poler |

(Continued)

FOREIGN PATENT DOCUMENTS

| DE | 8107675 U1 | 7/1981 |
|----|------------|--------|
| DE | 3439551 A1 | 4/1986 |

(Continued)

OTHER PUBLICATIONS

International Search Report and Written Opinion for Application No. PCT/IB2011/001067, mailed on Sep. 13, 2011, 13 pages.

(Continued)

*Primary Examiner* — Paul Prebilic
(74) *Attorney, Agent, or Firm* — AMO Groningen B.V.

(57) ABSTRACT

An intraocular lens for providing enhanced vision includes an optic having a clear aperture having an outer diameter. The optic has opposing first and second surfaces disposed about an optical axis, the first surface including a cross-sectional profile. The optic further includes central and outer zones that fill the entire clear aperture of the optic. The central zone is disposed about the optical axis having an outer diameter, the profile in the vicinity of the central zone having a constant radius of curvature or a radius of curvature that increases with increasing radius from the optical axis.

8 Claims, 5 Drawing Sheets

(56) References Cited

U.S. PATENT DOCUMENTS

| | | | |
|---|---|---|---|
| 4,254,509 A | 3/1981 | Tennant | |
| 4,254,510 A | 3/1981 | Tennant | |
| 4,316,293 A | 2/1982 | Bayers | |
| 4,319,564 A | 3/1982 | Karickhoff | |
| 4,338,005 A | 7/1982 | Cohen | |
| 4,340,283 A | 7/1982 | Cohen | |
| 4,370,760 A | 2/1983 | Kelman | |
| 4,377,873 A | 3/1983 | Reichert, Jr. | |
| 4,402,579 A | 9/1983 | Poler | |
| 4,403,353 A | 9/1983 | Tennant | |
| 4,404,694 A | 9/1983 | Kelman | |
| 4,409,691 A | 10/1983 | Levy | |
| 4,424,597 A | 1/1984 | Schlegel | |
| 4,446,581 A | 5/1984 | Blake | |
| 4,480,340 A | 11/1984 | Shepard | |
| 4,500,382 A | 2/1985 | Foster | |
| 4,504,982 A | 3/1985 | Burk | |
| 4,551,864 A | 11/1985 | Akhavi | |
| 4,556,998 A | 12/1985 | Siepser | |
| 4,560,383 A | 12/1985 | Leiske | |
| 4,593,981 A * | 6/1986 | Scilipoti | 351/159.41 |
| 4,605,409 A | 8/1986 | Kelman | |
| 4,605,411 A | 8/1986 | Fedorov et al. | |
| 4,629,460 A | 12/1986 | Dyer | |
| 4,629,462 A | 12/1986 | Feaster | |
| 4,636,049 A * | 1/1987 | Blaker | 351/159.41 |
| 4,637,697 A | 1/1987 | Freeman | |
| 4,642,112 A | 2/1987 | Freeman | |
| 4,655,565 A | 4/1987 | Freeman | |
| 4,673,406 A | 6/1987 | Schlegel | |
| 4,676,791 A | 6/1987 | LeMaster et al. | |
| 4,676,792 A | 6/1987 | Praeger | |
| 4,681,102 A | 7/1987 | Bartell | |
| 4,687,484 A | 8/1987 | Kaplan | |
| 4,687,485 A | 8/1987 | Lim et al. | |
| RE32,525 E | 10/1987 | Pannu | |
| 4,725,277 A | 2/1988 | Bissonette | |
| 4,734,095 A | 3/1988 | Siepser | |
| 4,778,462 A | 10/1988 | Grendahl | |
| 4,781,717 A | 11/1988 | Grendahl | |
| 4,787,903 A | 11/1988 | Grendahl | |
| 4,787,904 A | 11/1988 | Severin et al. | |
| 4,795,462 A | 1/1989 | Grendahl | |
| 4,798,608 A | 1/1989 | Grendahl | |
| 4,798,609 A | 1/1989 | Grendahl | |
| 4,828,558 A | 5/1989 | Kelman | |
| 4,834,748 A | 5/1989 | McDonald | |
| 4,863,539 A | 9/1989 | Lee et al. | |
| 4,898,461 A * | 2/1990 | Portney | 351/159.42 |
| 4,932,970 A | 6/1990 | Portney | |
| 4,995,714 A | 2/1991 | Cohen | |
| 4,995,715 A | 2/1991 | Cohen | |
| 4,997,442 A | 3/1991 | Barrett | |
| 5,016,977 A | 5/1991 | Baude et al. | |
| 5,019,097 A | 5/1991 | Knight et al. | |
| 5,047,052 A | 9/1991 | Dubroff | |
| 5,054,905 A | 10/1991 | Cohen | |
| 5,056,908 A | 10/1991 | Cohen | |
| 5,066,301 A | 11/1991 | Wiley | |
| 5,071,432 A | 12/1991 | Baikoff | |
| 5,078,742 A | 1/1992 | Dahan | |
| 5,089,023 A | 2/1992 | Swanson | |
| 5,096,285 A * | 3/1992 | Silberman | 351/161 |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,133,749 A | 7/1992 | Nordan | |
| 5,144,483 A | 9/1992 | Cohen | |
| 5,147,395 A | 9/1992 | Willis | |
| 5,147,397 A | 9/1992 | Christ et al. | |
| 5,184,405 A | 2/1993 | Cress | |
| 5,197,981 A | 3/1993 | Southard | |
| 5,201,763 A | 4/1993 | Brady et al. | |
| 5,203,790 A | 4/1993 | McDonald | |
| 5,217,491 A | 6/1993 | Vanderbilt | |
| 5,225,858 A | 7/1993 | Portney | |
| 5,229,797 A | 7/1993 | Futhey et al. | |
| 5,258,025 A | 11/1993 | Fedorov et al. | |
| 5,278,592 A | 1/1994 | Marie et al. | |
| 5,408,281 A | 4/1995 | Zhang | |
| 5,433,745 A | 7/1995 | Graham et al. | |
| 5,476,513 A | 12/1995 | Brady et al. | |
| 5,479,220 A | 12/1995 | Komatsu et al. | |
| 5,567,365 A | 10/1996 | Weinschenk, III et al. | |
| 5,571,177 A | 11/1996 | Deacon et al. | |
| 5,620,720 A | 4/1997 | Glick et al. | |
| 5,628,796 A | 5/1997 | Suzuki | |
| 5,652,638 A | 7/1997 | Roffman et al. | |
| 5,691,800 A | 11/1997 | Iki et al. | |
| 5,699,142 A | 12/1997 | Lee et al. | |
| 5,716,403 A | 2/1998 | Tran et al. | |
| 5,748,282 A | 5/1998 | Freeman | |
| 5,760,871 A | 6/1998 | Kosoburd et al. | |
| 5,796,462 A | 8/1998 | Roffman et al. | |
| 5,801,807 A | 9/1998 | Satake et al. | |
| 5,928,282 A | 7/1999 | Nigam | |
| 5,968,094 A | 10/1999 | Werblin et al. | |
| 6,015,435 A | 1/2000 | Valunin et al. | |
| 6,051,024 A | 4/2000 | Cumming | |
| 6,126,286 A * | 10/2000 | Portney | 351/159.14 |
| 6,129,759 A | 10/2000 | Chambers | |
| 6,142,625 A | 11/2000 | Sawano et al. | |
| 6,179,870 B1 | 1/2001 | Sourdille et al. | |
| 6,210,005 B1 * | 4/2001 | Portney | 351/161 |
| 6,235,055 B1 | 5/2001 | Chu | |
| 6,261,321 B1 | 7/2001 | Kellan | |
| 6,319,282 B1 | 11/2001 | Nishi | |
| 6,338,559 B1 | 1/2002 | Williams et al. | |
| 6,419,697 B1 | 7/2002 | Kelman | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,536,899 B1 | 3/2003 | Fiala | |
| 6,537,317 B1 | 3/2003 | Steinert et al. | |
| 6,547,822 B1 * | 4/2003 | Lang | 623/6.28 |
| 6,554,859 B1 * | 4/2003 | Lang et al. | 623/6.28 |
| 6,557,992 B1 | 5/2003 | Dwyer et al. | |
| 6,598,606 B2 | 7/2003 | Terwee et al. | |
| 6,609,793 B2 | 8/2003 | Norby et al. | |
| 6,705,729 B2 | 3/2004 | Piers et al. | |
| 6,709,102 B2 * | 3/2004 | Duppstadt | 351/159.46 |
| 6,802,605 B2 | 10/2004 | Cox et al. | |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,851,803 B2 | 2/2005 | Wooley et al. | |
| 6,899,425 B2 | 5/2005 | Roffman et al. | |
| 6,923,539 B2 | 8/2005 | Simpson et al. | |
| 6,923,540 B2 | 8/2005 | Ye et al. | |
| 6,986,578 B2 | 1/2006 | Jones | |
| 7,036,931 B2 | 5/2006 | Lindacher et al. | |
| 7,048,760 B2 | 5/2006 | Cumming | |
| 7,061,693 B2 | 6/2006 | Zalevsky | |
| 7,073,906 B1 | 7/2006 | Portney | |
| 7,137,702 B2 | 11/2006 | Piers et al. | |
| 7,156,516 B2 | 1/2007 | Morris et al. | |
| 7,188,949 B2 | 3/2007 | Bandhauer et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,441,894 B2 | 10/2008 | Zhang et al. | |
| 7,455,404 B2 | 11/2008 | Bandhauer et al. | |
| 7,455,407 B2 | 11/2008 | Neal et al. | |
| 7,475,986 B2 | 1/2009 | Dai et al. | |
| 7,615,073 B2 | 11/2009 | Deacon et al. | |
| 7,616,330 B2 | 11/2009 | Neal et al. | |
| 7,794,497 B2 | 9/2010 | Brady et al. | |

(56) References Cited

U.S. PATENT DOCUMENTS

| | | |
|---|---|---|
| 7,857,451 B2 | 12/2010 | Thibos et al. |
| 7,871,162 B2 | 1/2011 | Weeber |
| 8,382,281 B2 * | 2/2013 | Weeber ............... 351/159.11 |
| 8,480,228 B2 | 7/2013 | Weeber |
| 8,747,466 B2 * | 6/2014 | Weeber et al. ............ 623/6.28 |
| 8,770,745 B2 * | 7/2014 | Lindacher et al. ...... 351/159.05 |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0054358 A1 * | 3/2004 | Cox et al. ..................... 606/5 |
| 2004/0068317 A1 * | 4/2004 | Knight ...................... 623/6.48 |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0150790 A1 * | 8/2004 | Roffman et al. ............... 351/161 |
| 2004/0156014 A1 | 8/2004 | Piers et al. |
| 2004/0167622 A1 * | 8/2004 | Sunalp et al. ............... 623/6.12 |
| 2004/0230299 A1 | 11/2004 | Simpson et al. |
| 2005/0096226 A1 | 5/2005 | Stock et al. |
| 2005/0125056 A1 * | 6/2005 | Deacon et al. ............... 623/6.21 |
| 2005/0128432 A1 | 6/2005 | Altmann |
| 2005/0203619 A1 * | 9/2005 | Altmann ...................... 623/6.23 |
| 2005/0251254 A1 * | 11/2005 | Brady et al. ................. 623/6.37 |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0068453 A1 | 3/2006 | Altieri |
| 2006/0098162 A1 | 5/2006 | Bandhauer et al. |
| 2006/0098163 A1 | 5/2006 | Bandhauer et al. |
| 2006/0109421 A1 * | 5/2006 | Ye et al. ..................... 351/160 R |
| 2006/0116763 A1 | 6/2006 | Simpson |
| 2006/0116764 A1 | 6/2006 | Simpson |
| 2006/0116765 A1 | 6/2006 | Blake et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244916 A1 | 11/2006 | Guillon |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0231809 A1 | 9/2008 | Haigis |
| 2008/0269642 A1 * | 10/2008 | Deacon et al. ................. 600/587 |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0279048 A1 * | 11/2009 | Hong et al. ................. 351/161 |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0130888 A1 | 5/2010 | Deacon et al. |
| 2010/0161048 A1 | 6/2010 | Schaper, Jr. |
| 2012/0140166 A1 | 6/2012 | Zhao |

FOREIGN PATENT DOCUMENTS

| | | |
|---|---|---|
| EP | 226400 A2 | 6/1987 |
| EP | 227357 A2 | 7/1987 |
| EP | 0343067 A1 | 11/1989 |
| EP | 457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 | 2/2004 |
| EP | 1310267 B1 | 1/2008 |
| FR | 2745711 A1 | 9/1997 |
| WO | WO-8603961 A1 | 7/1986 |
| WO | WO9222264 A1 | 12/1992 |
| WO | WO9303409 A1 | 2/1993 |
| WO | WO-9507487 A1 | 3/1995 |
| WO | WO-9856315 A1 | 12/1998 |
| WO | WO0019906 A1 | 4/2000 |
| WO | WO-0111418 A1 | 2/2001 |
| WO | WO-0135868 A1 | 5/2001 |
| WO | 0163344 | 8/2001 |
| WO | WO-0154569 A1 | 8/2001 |
| WO | 01/82839 A1 | 11/2001 |
| WO | 01/89424 A1 | 11/2001 |
| WO | 0182839 | 11/2001 |
| WO | 02/21194 A2 | 3/2002 |
| WO | 0221194 | 3/2002 |
| WO | WO03009053 A1 | 1/2003 |
| WO | WO2004034129 A1 | 4/2004 |
| WO | 2004/090611 A2 | 10/2004 |
| WO | 2004090611 | 10/2004 |
| WO | WO2004096014 A2 | 11/2004 |
| WO | 2005/019906 A1 | 3/2005 |
| WO | 2005019906 | 3/2005 |
| WO | WO2006025726 A1 | 3/2006 |
| WO | WO-2006032263 A2 | 3/2006 |
| WO | WO2006047698 A1 | 5/2006 |
| WO | 2006/060477 A2 | 6/2006 |
| WO | 2006060477 | 6/2006 |
| WO | WO2006060480 A2 | 6/2006 |
| WO | WO-2007067872 A2 | 6/2007 |
| WO | WO2007092948 A1 | 8/2007 |
| WO | WO2007133384 A2 | 11/2007 |
| WO | 2008/045847 A2 | 4/2008 |
| WO | WO-2008083283 A2 | 7/2008 |
| WO | WO-2009020963 A1 | 2/2009 |
| WO | WO2009029515 A1 | 3/2009 |
| WO | WO2009076670 A1 | 6/2009 |
| WO | WO-2009137491 A1 | 11/2009 |
| WO | WO-2010009254 A1 | 1/2010 |
| WO | WO-2010009257 A1 | 1/2010 |

OTHER PUBLICATIONS

Piers P.A., et al., "Eye Models for the Prediction of Contrast Vision in Patients with New Intraocular Lens Designs," Optics Letters, 2004, vol. 29 (7), pp. 733-735, (Apr. 2004)

Terwee T., et al., "Visualization of the Retinal Image in an Eye Model With Spherical and Aspheric, Diffractive, and Refractive Multifocal Intraocular Lenses" Journal of Refractive Surgery, 2008, vol. 24 (3), pp. 223-232, (Mar. 2008).

Alfonso J.F., et al., "Prospective Study of the Acri.LISA bifocal Intraocular Lens," Journal of Cataract Refractive Surgery, 2007, vol. 33 (11), pp. 1930-1935, (Oct. 2007).

Canovas C., et al., "Hybrid Adaptive-Optics Visual Simulator," Optical Letters, 2010, vol. 35 (2), pp. 196-198, (Jun. 2010).

Cohen, Allen L., "Practical design of a bifocal hologram contact lens or intraocular lens," Applied Optics, 1992, 31 (19), 3750-3754, (Jul. 1992).

Co-pending U.S. Appl. No. 12/771,550, filed Apr. 30, 2010.

Diffractive Lenses for Extended Depth of Focus and Presbyopic Correction. Presentation from Wavefront Congress held on Feb. 15, 2008, Rochester, New York.

(56) References Cited

OTHER PUBLICATIONS

Doskolovich L.L., et al., "Special Diffractive Lenses," SPIE, 1992, vol. 1780, pp. 393-402, (Apr. 1993).
International Search Report for Application No. PCT/EP2008/061235, mailed on Mar. 5, 2009, 4 pages.
International Search Report for Application No. PCT/EP2009/051783, mailed on Apr. 28, 2009, 3 pages.
International Search Report for Application No. PCT/IB2009/005590, mailed on Sep. 30, 2009, 3 pages.
International Search Report for Application No. PCT/US08/073999, mailed on Dec. 3, 2008, 3 pages.
International Search Report for Application No. PCT/US09/042449, mailed on Nov. 5, 2009, 5 pages.
International Search Report for Application No. PCT/US2010/038167, mailed on Sep. 27, 2010, 2 pages.
International Search Report for Application No. PCT/US2010/061081, mailed on Apr. 6, 2011, 2 pages.
Liou H.L., et al., "Anatomically Accurate, Finite Model Eye for Optical Modeling," Journal of Optical Society of America, 1997, vol. 14 (8), pp. 1684-1695, (Aug. 1997).
Marsack J.D., et al., "Metrics of Optical Quality Derived From Wave Aberrations Predict Visual Performance," Journal of Vision, 2004, vol. 4 (4), pp. 322-328, (Apr. 2004).
Monsoriu J.A., et al., "Devil's Lenses," Optics Express, 2007, vol. 15 (21), pp. 13858-13864, (Oct. 2007).
Norrby S., et al., "Model Eyes for Evaluation of Intraocular Lenses," Applied Optics, 2007, vol. 46 (26), pp. 6595-6605, (Sep. 2007).
Piers P.A., et al., "Theoretical Comparison or Aberration-Correcting Customized and Aspheric Intraocular Lenses," Journal of Refractive Surgery, 2007, vol. 23 (4), pp. 374-384, (Apr. 2007).
Siedlecki D., et al., "Radial Gradient index Intraocular Lens: a Theoretical Model," Journal of Modern Optics, 2008, vol. 55 (4-5), pp. 639-647, (Feb. 2010).
U.S. Appl. No. 12/129,155, filed May 29, 2008.
U.S. Appl. No. 11/618,325, filed Dec. 29, 2006 (Brady et al).
U.S. Appl. No. 11/618,411, filed Dec. 29, 2006(Bradyetai).
U.S. Appl. No. 12/109,251, filed Apr. 24, 2008.
Van Meeteren A., "Calculations on the Optical Modulation Transfer Function of the Human Eye for White Light," Optica Acta, 1974, vol. 21 (5), pp. 395-412, (Nov. 2010).
Vanden Berg T.J., "Analysis of Intraocular Straylight, Especially in Relation to Age," Optometry and Vision Science, 1995, vol. 72 (2), pp. 52-59, (Feb. 1995).
Villegas E.A., et al., "Correlation between Optical and Psychophy, Sical Parameters as a Function of Defocus," Optometry and Vision Science, 2002, vol. 79 (1), pp. 60-67, (Jan. 2002).
Co-pending U.S. Appl. No. 12/503,267, filed Jul. 15, 2009.
European Search Report for Application No. EP11165087, mailed on Jul. 22, 2011, 6 pages.
European Search Report for Application No. EP89304883, mailed on Sep. 3, 1990, 1 page.
International Preliminary Report on Patentability and Written Opinion for Application No. PCT/EP2008/061235, mailed on Mar. 2, 2010, 7 pages.
International Preliminary Report on Patentability and Written Opinion for Application No. PCT/EP2009/051783, mailed on Jun. 8, 2010, 6 pages.
International Preliminary Report on Patentability and Written Opinion for Application No. PCT/IB2009/005590, mailed on Sep. 6, 2011, 11 pages.
International Preliminary Report on Patentability and Written Opinion for Application No. PCT/US09/034555, mailed on Aug. 24, 2010, 8 pages.
International Preliminary Report on Patentability and Written Opinion for Application No. PCT/US09/042449, mailed on Nov. 17, 2010, 13 pages.
International Preliminary Report on Patentability and Written Opinion for Application No. PCT/US2008/073999, mailed on Mar. 2, 2010, 9 pages.
International Preliminary Report on Patentability for Application No. PCT/US08/061180, mailed on Oct. 27, 2009, 1 page.
International Preliminary Report on Patentability for Application No. PCT/US2009/038469, mailed on Sep. 28, 2010, 1 page.
International Search Report and Written opinion for Application No. PCT/US08/061180, mailed on Sep. 5, 2008, 10 pages.
International Search Report and Written opinion for Application No. PCT/US09/038469, mailed on Aug. 10, 2009, 12 pages.
International Search Report and Written Opinion for Application No. PCT/US2011/026193, mailed on Jun. 7, 2011, 17 pages.
International Search Report for Application No. PCT/US09/034555, mailed on May 18, 2009, 5 pages.
International Search Report for Application No. PCT/US2010/061017, mailed on Jun. 16, 2011, 7 pages.
International Search Report for Application No. PCT/US2010/061042, mailed on Mar. 31, 2011, 3 pages.
International Search Report for Application No. PCT/US2010/061081, mailed on Jun. 6, 2011, 7 pages.
International Search Report for Application No. PCT/US2011/043119, mailed on Feb. 15, 2012, 6 pages.
WO0154569 Machine Translation, Manfred Tetz and Stephan Schruender, May 12, 2000.

\* cited by examiner

MULTIZONAL LENS WITH EXTENDED DEPTH OF FOCUS

RELATED APPLICATION

This application is a continuation-in-part application of, and claims prior to, U.S. patent application Ser. No. 11/845,682, filed Aug. 27, 2007, the entire contents of each of which applications are hereby incorporated by reference in their entirety for all purposes as if fully set forth herein.

FIELD OF THE INVENTION

The present invention relates to devices and methods for enhancing vision of a subject and, more particularly, to multizonal ophthalmic lenses and methods of use thereof for enhancing vision of a subject.

BACKGROUND OF THE INVENTION

Intraocular lenses and other ophthalmic devices are used to restore and correct vision. For example, monofocal intraocular lenses may be used to replace the natural lens of an eye that has developed cataracts. The simplest type of monofocal intraocular lens is spherical lens in which both optical surfaces have a spherical profile. More recently, aspheric lenses have been used to enhance the visual acuity of intraocular lenses. Such aspheric lenses may be used to at least partially correct for aberrations that are produced by an opposing spherical surface and/or aberrations produced by the eye itself (e.g., positive spherical aberrations produced by the cornea of most human eyes). Examples of such lens designs are described in U.S. Pat. Nos. 6,609,793 and 7,137,702, which are herein incorporated by reference in their entirety. Lenses may also be configured to correct for chromatic aberrations inherent in most refractive lenses, for example, through the use of diffractive phase plates (e.g., U.S. Pat. Nos. 4,637,697, 5,121,979, and 6,830,332 and U.S. Patent Application Number 2004/0156014 and 2006/0098163, all of which are also herein incorporated by reference in their entirety).

When spherical intraocular lenses are used, a practitioner may, based on pre-operative ocular measurement, select a lens power that would make a subject somewhat myopic, for example choosing a lens power that provides a subject the best MTF performance or the best visual acuity for objects located at the so called "hyperfocal distance". One advantage of this approach is an increased likelihood that the subject will have spectacle-free vision for at least one distance or range of distances. That is, if the estimated lens power is incorrect and the intraocular lens is too strong—resulting in a myopic condition—then subject will need correction of distant vision, but will have near or intermediate vision without the use of spectacles or contact lenses. Additionally, if the lens power is selected to give the subject the best MTF performance or best visual acuity for objects located at the hyperfocal distance, the subject generally has a larger range of distances over which objects will be reasonably clear, without the use of spectacles or contact lenses. The increased range provided by choosing the lens power based on the hyperfocal distance may be considered as a type of pseudo-accommodation, in that the resulting vision performance over a range of distances resembles the vision provided by the eye's natural lens prior to the onset of presbyopia.

One potential drawback to selecting the optical power of an intraocular lens based on the hyperfocal distance is that visual acuity for nighttime driving may be reduced, since the best lens performance is for objects located at the hyperfocal distance, rather than at optical infinity. However, most of the objects within the field of view under nighttime driving conditions are at optical infinity and are, therefore, slightly defocused. Since the pupil is fully dilated under these conditions, spherical aberrations may further reduce visual acuity. The effects of spherical aberrations may, however, be reduced by using aspheric lens surfaces that are configured to reduce, correct, or compensate for spherical aberrations of the lens and/or cornea.

Regardless of in-focus condition selected (e.g., at optical infinity or at the hyperfocal distance), aspheric lens surfaces serve to provide an improved visual outcome. This is because, as compared to a substantially equivalent spherical lens, aspheric lenses generally provide better visual acuity or MTF performance at all distances, and not simply at the distance corresponding to the best-focus condition. However, while an aspheric lens with a power selected for the hyperfocal distance generally provides better nighttime driving vision than a spherical lens, the visual acuity will still be reduced compared to the performance when the lens power is selected to provide best-focus at optical infinity.

Accordingly, improved monofocal ophthalmic lenses are needed that will provide both increased visual acuity under nighttime driving conditions and, under other lighting conditions, provide the relatively large depth of focus that is possible by selecting a lens power based on a hyperfocal distance.

SUMMARY OF THE INVENTION

Embodiments of the present invention are generally directed to devices and methods for providing an eye with enhanced visual performance and/or visual acuity under certain visual and/or lighting conditions, while simultaneously providing a relatively large depth of field or depth of focus under other visual and/or lighting conditions. For example, an outer portion or zone of an optic of an intraocular lens may be configured to reduce, compensate, or cancel a spherical aberrations and/or other higher order monochromatic aberrations and/or chromatic aberrations when a pupil of an eye is relatively large (e.g., under typical nighttime driving conditions), while an inner or central portion or zone of the same optic may be configured to provide better depth of field or depth of focus when the pupil is relatively small (e.g., under typical indoor or outdoor lighting conditions or under typical reading conditions). Alternatively or additionally, the outer zone may be configured to provide the best visual acuity or optical performance for objects at optical infinity, while the inner or central zone is configured to provide the best visual acuity or optical performance for closer objects, for example, objects at a hyperfocal distance from the eye. The inner or central zone of the same optic may include opposing spherical surfaces that provide a greater depth of field or depth of focus than the outer zone of the optic. Alternatively, the inner or central zone may be configure have an enhanced depth of field or enhanced depth of focus that is greater than that of a substantially equivalent spherical zone (e.g., an inner or central zone having a depth of focus that is greater than that of a spherical zone having an optical power equal to an optical power or average optical power of the inner or central zone). Exemplary embodiments of the invention presented herein are generally directed to intraocular lenses; however, embodiments of the invention may also be extended to other types of ophthalmic lenses and devices, such as corneal inlays or onlays, phakic lenses, laser vision correction (e.g., LASIK and PRK procedures), contact lenses, and the like.

One aspect of the present invention involves an ophthalmic device, such as an intraocular lens, comprising an optic having a variation in optical power over an entire clear aperture of the lens that is less than a predetermined amount and that is less than the add power of a typical refractive or diffractive multifocal intraocular lens (e.g., less than about 2 Diopters or 1.5 Diopters). The optic has an anterior surface and an opposing posterior surface, the surfaces disposed about an optical axis. The optic further comprises a central zone having a plurality of optical powers that progressively vary between a first optical power at a center of the central zone and a second optical power at a periphery of the central zone, wherein the absolute value of the difference between the first optical power and the second optical power is within a relatively small range compared to the add power of a typical refractive or diffractive multifocal intraocular lens (e.g., between about 0.25 Diopter and about 2 Diopters). The ophthalmic devices also comprises an outer zone disposed about the central zone, the outer zone comprising a third optical power and optionally an optical aberration to compensate or reduce a similar aberration of the cornea or eye of a subject or group of subject. The optical aberration may be a chromatic aberration or a monochromatic aberration such as spherical aberration, coma, or astigmatism.

Another aspect of the present invention involves a method of making an intraocular lens or other ophthalmic device, the method comprising forming an anterior surface and an opposing posterior surface, the surfaces being disposed about an optical axis and providing a clear aperture. The method also comprises forming a central zone comprising a plurality of optical powers that progressively vary between a first optical power at a center of the central zone and a second optical power at a periphery of the central zone. The method further comprises forming outer zone disposed about the central zone, the outer zone comprising a third optical power and an optionally an optical aberration. The optic has a variation in optical power over the entire clear aperture that is less than a predetermined amount and that is less than the add power of a typical multifocal intraocular lens (e.g., less than 3 Diopters or 4 Diopters, or between about 0.25 Diopter and about 2 Diopters).

Each and every feature described herein, and each and every combination of two or more of such features, is included within the scope of the present invention, provided that the features included in such a combination are not mutually inconsistent.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

As used herein, the term "optical power" means the ability of a lens or optic, or portion thereof, to converge or diverge light to provide a focus (real or virtual) when disposed within a media. When used in conjunction with an intraocular lens, the optical power is that of the intraocular lens when disposed within a media having a refractive index of 1.336 (generally considered to be the refractive index of the aqueous and vitreous humors of the human eye). In any event, the optical power is generally specified in units of reciprocal meters ($m^{-1}$) or Diopters (D). See ISO 11979-2, which is herein incorporated by reference in its entirety. As used herein the term "focal length" means the reciprocal of the optical power, and is typically expressed in units of millimeters (mm). As used herein the term "power", when used in reference to an optic or lens, means "optical power". As used herein, the term "refractive power" or "refractive optical power" means the power of a lens or optic, or portion thereof, attributable to refraction of incident light. As used herein, the term "diffractive power" or "diffractive optical power" means the power of a lens or optic, or portion thereof, attributable to diffraction of incident light into one or more diffraction orders. Except where noted otherwise, the optical power of a lens or optic is from a reference plane associated with the lens or optic (e.g., a principal plane of an optic). When used in conjunction with optical power in Diopters, the term "about" or "approximately" means within plus or minus 0.25 Diopters.

Accept where noted otherwise, the phrase "optical power of an optic" or "optical power of a lens", or similar such phrase, means a paraxial power of the optic or lens (i.e., the power near the optical axis of the optic or lens for rays of collimated light parallel to the optical axis). As used herein, the terms "power" or "optical power", when used in reference to a portion or zone of an optic or lens, means a local power of the portion or zone, or some portion thereof. As used herein, a "spherical optic" means an optic having anterior and posterior surfaces each described by a sphere having a constant radius of curvature and is considered to have a paraxial power at the optical axis thereof and local powers over the optic that increase with increasing radius from the optical axis as a result of spherical aberration. This increase of power with increasing radius of the spherical optic is a "positive spherical aberration". As used herein, an "aspheric optic" has at least one optical surface with a shape that deviates from a spherical shape, and is considered to have a paraxial power at the optical axis thereof and local powers that may, with increasing radius from the optical axis, increase (e.g., multifocal optic or an optic with enhanced depth of focus), remain constant (e.g., an aspheric optic configured to eliminate or cancel a spherical aberration of an opposing optical surface of the optic), or decrease (e.g., an optic configured to reduce, compensate, or cancel a spherical aberration of an opposing optical surface of the optic and/or of an optical system or eye into which the optic is placed).

As used herein, the term "near vision" means vision produced by an eye that allows a subject to focus on objects or planes that are relatively close to the subject, for example, within a range of about 25-40 cm or at a distance at which a subject would generally place printed material for the purpose of reading. As used herein, the term "distant vision" means vision produced by an eye that allows a subject to focus on objects or planes that are located at least 6 meters away from the eye. As used herein, the term "intermediate vision" means vision of objects at approximately 40 centimeters to approximately 1.5 meters from the eye or spectacle plane.

As used herein, the term "hyperfocal distance" means a distance at which, for an emmetropic eye, an add power of 0.4 Diopters in the spectacle plane of the eye provides a best MTF performance or a best visual acuity (e.g., a visual acuity of 20/20 or better, based on the standard Snellen test for visual acuity). For example, in a human eye with an axial length (AL) of 25 mm, the hyperfocal distance is 2.5 meters from the eye or about 2.5 meters from the eye, where "about" means within plus or minus 0.25 meters. As used herein, the term "emmetropic vision" or "emmetropia" means a state of vision in which an object at a distance of about 6 meters from an eye produces a visual acuity of 20/20 or better with the eye lens in a neutral or relaxed state. As used herein, the term "emmetropic eye" means an eye producing emmetropic vision. As used herein, the term "best visual acuity" means, for a given state of accommodation of an eye, a visual acuity experienced by a subject that cannot be improved by moving an object or plane further away from, or closer to, the subject. As used herein, the term "best MTF performance" means, for a given focus condition, a MTF performance produced by a lens or optical system (including an ocular system) that cannot be improved by moving an object or plane further away from, or closer to, the lens or ocular system.

As used herein, the term "clear aperture" means the opening of a lens or optic that restricts the extent of a bundle of light rays from a distant light source that can imaged or focused by the lens or optic. The clear aperture is usually circular and specified by its diameter. Thus, the clear aperture represents the full extent of the lens or optic usable in forming a image of an object, or in focusing light from a distant point source to a single focus or, in the case of a multifocal optic or lens, to a plurality of predetermined foci. It will be appreciated that the term "clear aperture" does not denote or imply a particular clarity or transmissivity of an optic or lens. For example, an optic may have a clear aperture that is approximately equal to the diameter of the optic, irrespective of whether or not a dye is used that reduces the transmission of light.

As used herein, the term "depth of field" (DOF) means a range of distances from an eye or subject over which an acceptable visual or optical performance is provided—for example, over which an acceptable amount of defocus, an acceptable MTF performance, or an acceptable visual acuity is provided. As used herein, the term "extended DOF," as applied to an optic, means that the depth of field of the optic, or an optical system of which the optic is used, is greater than the depth of focus provided by a reference spherical optic made of the same material, and having the same paraxial power and radius of curvature for the anterior and posterior surfaces, as the optic having the extended DOF. As used herein, the term "depth of field" means the range of distances at or near an image plane or retina that corresponds to the DOF.

As used herein, the term "optical infinity" means a distance of 6 meters or greater from an optic, lens, lens system, or eye.

Figure 1:
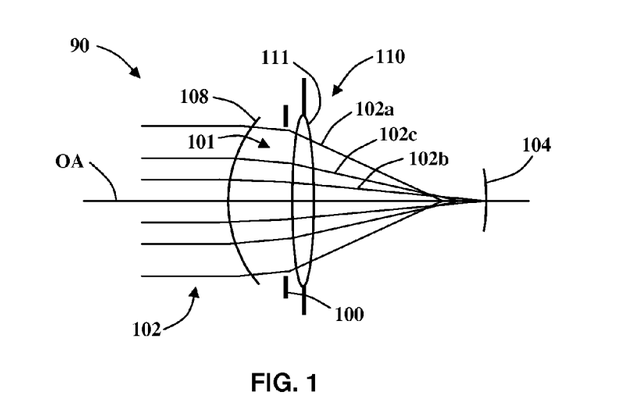
FIG. 1 is a side view of an intraocular lens comprising spherical surfaces and disposed within an eye.

Referring to FIG. 1, an eye 90 is generally disposed about an optical axis OA and comprises an iris 100 forming a pupil 101 through which a plurality of rays 102 from a distant object or point source enter the pupil 101 and are generally focused onto a retina 104 by a cornea 108 and an intraocular lens 110 comprising an spherical optic 111. For simplicity, other portions and elements of the eye 90 apart from those shown in FIG. 1 have been left out. The combination of the spherical surfaces of the intraocular lens 110 and the corneal surface shape (which typically has a positive spherical aberration) cause peripheral ray 102a to focus closer to the intraocular lens 110 than does inner or paraxial ray 102b. The focal length of the intraocular lens 110 may be represented by an intermediate ray 102c that focuses on the optical axis OA at a location intermediate to the foci of the rays 102a, b. The ray 102c may correspond to a ray that intercepts the optical axis OA at a plane located at the so-called "circle of least" confusion, although other criteria may be used for determining and/or defining the focal length of the intraocular lens 110 (e.g., criteria based on the paraxial focal length represented by the paraxial ray 102b).

When the optical power of an optic or optical system varies continuously with distance from the optical axis OA (e.g., as illustrated in FIG. 1), the range of resulting foci along the optical axis OA may be related to an increased depth of focus or DOF of the optic or optical system. In the case of the intraocular lens 110, the optical power of the lens is selected so that the paraxial ray 102b is focused onto the retina 104. Thus, at least some light from the distant point source represented in FIG. 1 is focused onto the retina 104 so that the intraocular lens 110 provides distant vision that is clinically equivalent to, or at least similar to, that provided if the intraocular lens 110 were configured to focus the ray 102c onto the retina 104.

Figure 2:
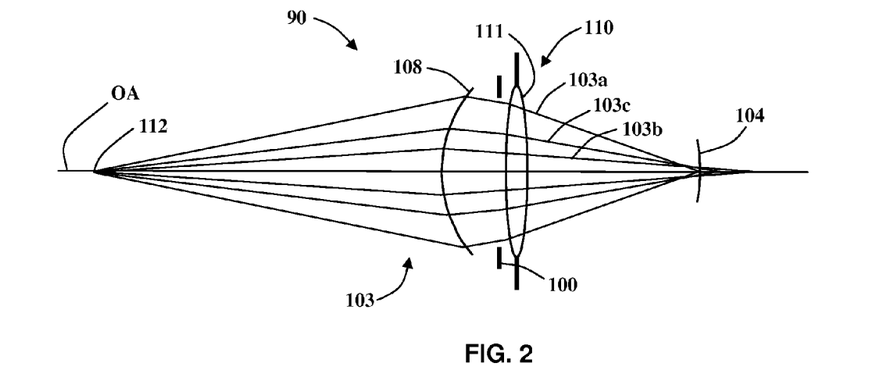
FIG. 2 is a side view of the intraocular lens of FIG. 1 in which an object or point source is disposed nearer the eye.

With further reference to FIG. 2, an advantage of the arrangement illustrated in FIG. 1 is that an object or point source 112 located at a hyperfocal distance from the eye 90 is also just focused by the optic 111 and cornea 108. As illustrated, a plurality of rays 103 from object source 112 are focused by the cornea 108 and the intraocular lens 110 (e.g., rays 103a-c). The peripheral ray 103a is just focused onto the retina 104, so that an object or point source disposed at the hyperfocal distance is perceived with similar visual acuity as a distant point source at optical infinity. Put another way, the hyperfocal distance may represent the distance at which the circle of confusion caused by the paraxial ray 103b is just within an acceptable limit. Such an arrangement allows the spherical intraocular lens 110 and/or cornea 108 to provide a pseudo-accommodation in which both distant objects and objects located at intermediate distances (e.g., at or near the hyperfocal distance) are suitably resolved by the eye 90. If the power of the optic 111 had been selected so that the ray 102c (from a distant source) focused on the retina 104, this may have provided better visual acuity for objects at optical infinity or distant objects; however, the object source 112 would have been blurred beyond an acceptable limit, resulting in a lower overall depth of focus.

Figure 3:
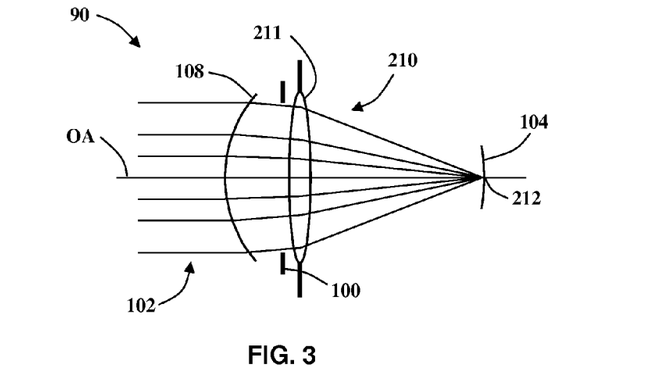
FIG. 3 is a side view of an intraocular lens comprising at least one aspheric surface configured to reduce a spherical aberration of the eye.

Referring now to FIG. 3, an aspheric intraocular lens 210 is illustrated that comprises an optic 211 in which at least one of the surfaces is aspheric, such that all the rays 102 from a distant object or point source come to a common focus 212 on the surface of the retina 104 after passing through the cornea 108 and the optic 211. In such arrangements, the surfaces of the optic 211 are generally configured such that the optic 211 has a negative spherical aberration that is selected to compensate or cancel a positive spherical aberration produced by a spherical surface of the optic 211 and/or produced by a spherical aberration of the cornea 108. Additionally or alternatively, the intraocular lens 210 may be configured to comprise another monochromatic aberration that compensates, reduces, or cancels a substantially opposite aberration of the cornea 108 and/or a spherical surface of the optic 211. As discussed in U.S. Pat. No. 6,609,793, the cornea 108 may represent an average model cornea (e.g., based on a population having a common characteristic). In such instances, the surfaces of the optic 211 may have a negative spherical aberration that partially or completely compensates for a spherical aberration of the cornea 108. The population may, for example, represent patients that are candidates for a cataract surgery, patients within a certain age group, and/or having a common or similar aberration or set of aberrations.

Figure 4:
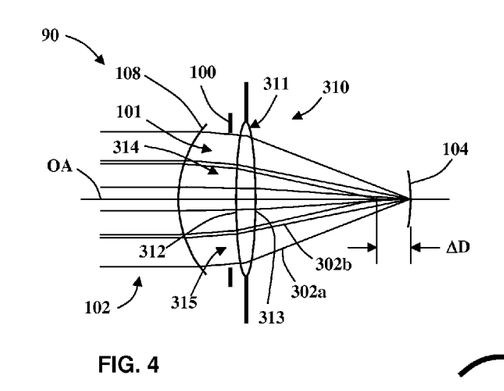
FIG. 4 is a side view of an intraocular lens comprising a central zone and a peripheral zone according to an embodiment of the present invention.
Figure 5:
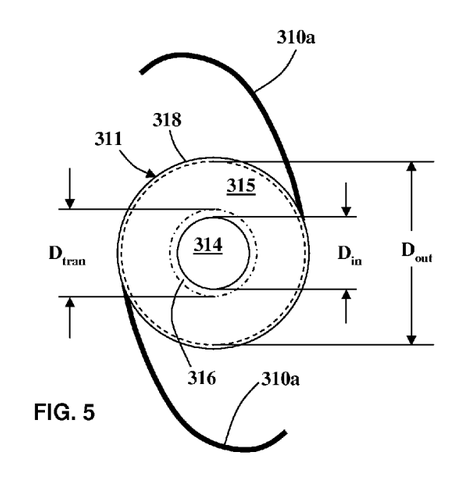
FIG. 5 is a front view of the intraocular lens of FIG. 4.

Referring to FIGS. 4 and 5, an intraocular lens 310 according to an embodiment of the present invention is disposed within a human or animal eye. The intraocular lens 310 comprises an optic 311 that is spherical in shape and/or is configured to provide an extended DOF (e.g., similar to that illustrated for the intraocular lens 110) under certain lighting conditions, while also providing enhanced visual acuity (e.g., similar to that produced by the aspheric intraocular lens illustrated for the intraocular lens 210) under other lighting conditions. The optic 311 has a clear aperture over which light from a distant object is focused onto the retina 104, and outside which light is not focused onto the retina 104. The optic 311 includes an anterior surface 312 and an opposing posterior surface 313, the surfaces 312, 313 being disposed about an optical axis OA. The intraocular lens 310 may also include haptics 310a that are generally configured to support the intraocular lens 310 in the eye 90 and/or to center the intraocular lens 310 within the eye 90. In certain embodiments, the haptics 310a may be replaced or supplemented by a more complex support structure, for example, for allowing an accommodating intraocular lens to interact with the capsular bag, zonules, and/or ciliary muscle (not shown) of the eye 90.

The optic 311 comprises a central or inner zone 314 disposed about the optical axis OA and having an outer diameter $D_{in}$. The optic 311 further comprises an outer zone 315 disposed about, and adjacent to, the inner zone 314 and having an outer diameter $D_{out}$ and an inner diameter $D_{in}$, so that the zones 314, 315 fill the entire clear aperture of the optic 311. Alternatively, the outer diameter $D_{out}$ of the outer zone 315 is less than the diameter of the clear aperture of the optic 311, so that the optic 311 contains other optical features in addition to those of the zones 314, 315. In the illustrated embodiment, the zone 314 is circular when viewed from the anterior side (e.g., as illustrated in FIG. 5). Alternatively, the zone 314 may be annular when viewed from the anterior side.

In the illustrated embodiment, the outer diameter $D_{out}$ is equal to the diameter of the clear aperture of the optic 311, which may be equal to or substantially equal to the diameter of the optic 311. Optionally, the outer diameter $D_{out}$ may be smaller than the outer diameter of the optic 311, as illustrated by the dash-dotted circle in FIG. 5. For example, the intraocular lens 310 may include a peripheral edge 318 configured to block or scatter light and, therefore, not focus light or form an image on the retina 104. The peripheral edge 318 may be configured to reduce scatter from light sources at the periphery of the field of view of a subject into which the lens 210 is implanted. Thus, the glare reducing peripheral edge 318 may slightly reduce the size of the clear aperture of the optic 311.

Figure 6:
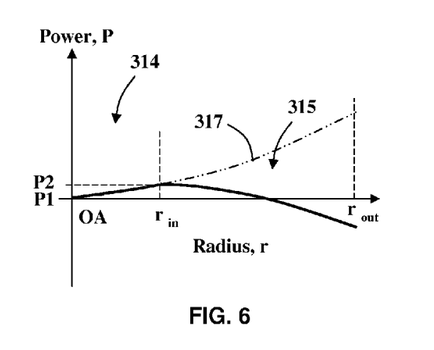
FIG. 6 is a plot of power of the intraocular lens shown in FIGS. 4 and 5 according to an embodiment of the present invention.

With further reference to FIG. 6, the central zone 314 may include a plurality of optical powers that progressively vary between a first optical power P1 at or near a center of the central zone 314 and a second optical power P2 at or near a periphery of the central zone 314. The power P1 may be configured to provide distant vision, or may be configured to have a power that is greater than a power to provide distant vision, for example, a power that is suitable to provide a best visual acuity or best MTF for intermediate vision or for objects located at a hyperfocal distance (e.g., at 2.5 meters from the eye 90). In the plot shown in FIG. 6, $r_{in}$ is equal to the outer radius of the central zone 314 and is equal to $D_{in}/2$, while $r_{out}$ is equal to the outer radius of the outer zone 315 and is equal to $D_{out}/2$. P1 may be a positive optical power, a negative optical power, or even zero optical power. Thus, the horizontal axis shown in this plot, and the other plots shown herein, generally intersect the vertical axis at some off-set value that is non-zero. As shown in FIG. 6, the power of the outer zone 315 may progressively decrease from the optical power P2 with increasing radius from the optical axis OA, so that the optic 311 has a negative spherical aberration in the vicinity of the outer zone 315 (e.g., to reduce, correct, or cancel a positive spherical aberration of the cornea 108). In the illustrated embodiment, the power within the outer zone 315 decreases out to radius $r_{out}$ to a value that is less than P1. Alternatively, the radial decrease in power within the outer zone 315 may be less than that shown in the illustrated embodiment, for example, to a value at $r_{out}$ that is greater than or equal to P1.

As a reference, the dotted/dashed reference curve 317 represents the power variation with radius from the optical axis OA of a reference spherical optic having a paraxial power equal to the first optical power P1 of the optic 311, wherein the reference spherical optic is made of the same material and comprises anterior and posterior surfaces each having the radius of curvature equal to the radius of curvature of corresponding anterior/posterior surfaces 312, 313 of the optic 311 at the optical axis OA. The absolute value of the difference between the first optical power P1 and the second optical power P2 (e.g., {P2-P1}) is generally less than the add power of a typical multifocal intraocular lens (e.g., less than 3 or 4 Diopters, or less than about 2 Diopters).

For example, the absolute difference between P1 and P2 is generally between about 0.1 Diopter and about 1.5 Diopter or between about 0.25 Diopter and about 1 Diopter. The power P1 may be a paraxial power or a base power of the optic 311, and/or the central zone 314, and may be selected to provide distant vision or emmetropia for an animal or human subject. Additionally or alternatively, the central zone 314 may comprise spherical surfaces 312, 313, wherein the power P2 is equal to or substantially equal to the power of the reference spherical optic represented by the reference curve 317 at radius $r_{in}$.

In certain embodiments, the central zone 314 may comprise a plurality of distinct powers that are produced through the use of a refractive and/or diffractive surface profile. For example, the central zone may comprise a diffractive grating or phase plate that produces two distinct foci. In general, the difference in optical power between the two foci is relatively small (e.g., less than or equal to about 1 Diopter, 1.5 Diopters, or 2 Diopters), although larger Diopter differences may be incorporated if a multifocal effect is desired. In some embodiments, a relatively small difference in optical power between the two foci may be used to provide an extended depth of focus, for example, as disclosed in co-pending U.S. Provisional Patent Application No. 60/968,250, which is herein incorporated by reference in its entirety.

The profile of one or both surfaces 312, 313 may be configured to provide a radial power profile that is different from that shown in FIG. 6, but that also provides both relatively large depth of focus performance at certain pupil sizes of the iris 100 and relatively high visual acuity or MTF performance at other pupil sizes. For example, referring to FIG. 7, the central zone 314 has a radial power profile that continuously increases with increasing radius from the optical axis OA, but at a rate that is greater than that of the reference curve 317 (i.e., greater than the power variation with radius of the reference spherical optic having a paraxial power P1 equal to that of the optic 311). In some embodiments, the power profile of the central zone 314 may be configured to increase depth of focus by having a power that decreases with increasing radius from the optical axis OA, for example, by having a positive spherical aberration.

Figure 7:
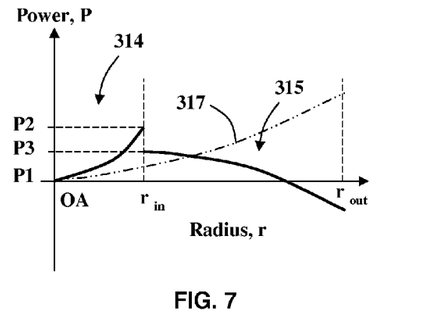
FIG. 7 is a plot of power of the intraocular lens shown in FIGS. 4 and 5 according to another embodiment of the present invention.

The outer zone 315 of optic 311 shown in FIG. 7 comprises a third optical power P3 that may be equal to P1 or P2, between P1 and P2, or outside the range between P1 and P2. Either or both of the zones 314, 315 may include a monochromatic and/or chromatic aberration that is selected to improve vision when the pupil 101 is relatively large (e.g., under low light conditions or typical room light conditions). For example, at least one of the surfaces 312, 313 in the vicinity of the outer zone 315 may be configured so that the zone 315 has a negative spherical aberration that at least partially compensates for a positive spherical aberration of the cornea and/or for a positive spherical aberration of one or both of the surfaces of the optic 311.

Figure 8:
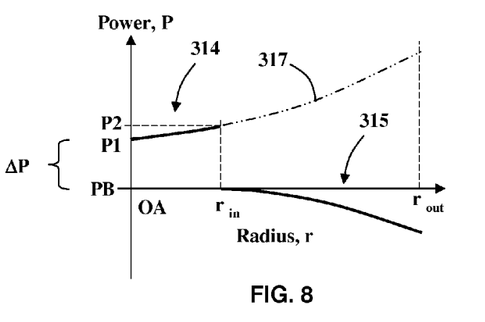
FIG. 8 is a plot of power of the intraocular lens shown in FIGS. 4 and 5 according to yet another embodiment of the present invention.

Referring to FIG. 8, in certain embodiments, the outer zone 315 of the optic 311 is configured to have a base power PB that produces emmetropia or distant vision when the optic 311 is disposed within the eye 90, while the central zone 314 is configured to have a higher power that provides intermediate vision or provides a best visual acuity or MTF performance for objects or planes located at a hyperfocal distance, for example at a distance of 2.5 meters from the eye 90 or about 2.5 meters from the eye 90. In the illustrated embodiment, the outer zone 315 has the base power PB at radius $r_{in}$ from the optical axis OA, and the power in the outer zone 315 monotonically decreases with increasing radius out to outer radius $r_{out}$. As discussed above, the decreasing power of the outer zone 315 may be configured to provide a negative spherical aberration that reduces or cancels a positive spherical aberration of the cornea 108. Alternatively, the power may be constant with radius between $r_{in}$ to $r_{out}$, whereby the optic 311 produces no spherical aberration within the outer zone 315. The central zone 314 in the illustrated embodiment has a power P1 at the optical axis OA and that increases to a power P2 at radial distance $r_{in}$. The difference between the power P1 and PB defines the power difference ΔP between the zones 314, 315. The power difference ΔP is generally small compared to the add power of a typical multifocal lens. For example, the power difference ΔP may be about 0.4 Diopters, so that the power of the central zone 314 is configure to provide a best visual acuity or best MTF performance at a hyperfocal distance of about 2.5 meters from the eye 90, while the outer zone 317 is configure to provide a best visual acuity or best MTF performance at distances greater than or equal to 6 meters from the eye 90 or at an optical infinity from the eye 90. Alternatively, power difference ΔP may be greater than or equal 0.4 Diopter and less than or equal to 1 Diopter, or greater than or equal 1 Diopter and less than or equal to 1.5 Diopters.

In the illustrated embodiment, the power variation of the central zone 314 matches that of a spherical optic having a paraxial power of P1; however, the variation of power of the central zone 314 may be aspheric in shape, for example, configured to produce an enhanced depth of focus that is greater than that of a spherical lens have a paraxial power equal to P1 of the optic 311.

Figure 9:
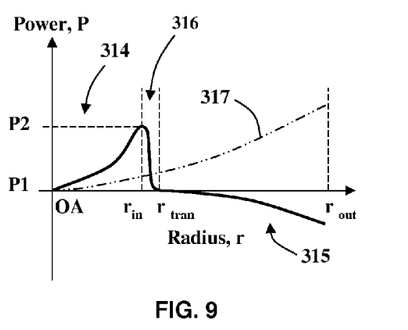
FIG. 9 is a plot of power of the intraocular lens shown in FIGS. 4 and 5 according to yet another embodiment of the present invention.

Referring again to FIG. 5, and with additional reference to FIG. 9, the optic 311 may further comprise an intermediate or transition zone 316 disposed between the central and outer zones 314, 315 (optionally indicated by the dashed circle in FIG. 5). In such embodiments, the central zone 314 has outer diameter $D_{in}$, the transition zone 316 has inner diameter $D_{in}$ and an outer diameter $D_{tran}$, and the outer zone 315 has an inner diameter $D_{tran}$ and outer diameter $D_{out}$. The parameter $r_{tran}$ shown in FIG. 9 is equal to $D_{tran}/2$. In such embodiments, one of the surfaces 312, 313 in the vicinity of the intermediate zone 316 may have a radial profile that is describe by a polynomial and/or spline that may be selected to smoothly blend the at least one of the surfaces of the zones 314, 315. In such cases, the outer diameter $D_{in}$ of the central zone 314 may or may not be clearly delineated. Thus, the transition zone 316 may be configured to reduce glare and light scatter by the optic 311. Where the transition zone 316 is configured to smoothly blend between zones 314, 315, and as illustrated in FIGS. 5 and 9, the transition zone 316 has a radial extent or area that is smaller than that of either of the zones 314, 315. For example, the transition zone 316 may have a radial extent that is less than or equal to 20% of the radial extent of either the of the zones 314, 315, or less than or equal to 10% of the radial extent of either the of the zones 314, 315

Optionally, the intermediate zone 316 may be utilized to further enhance the performance of the intraocular lens 310 in some way. For example, the intermediate zone 316 may be configured to provide better performance when the intraocular lens 310 is decentered or tilted after placement within an eye, as disclosed in U.S. Patent Application Number 2004/0106992, which is herein incorporated by reference in its entirety). Alternatively, the intermediate zone may be used to control halo effects, for example, as disclosed in U.S. Patent Application Number 2006/098163. The intermediate zone 316 in the illustrated in FIG. 9 has a power that smoothly varies from the power P2 at radius $r_{in}$ to a power of P1 at the radius $r_{tran}$. In general, the optical power at the radius $r_{in}$ may be different than P1, for example, some predetermined power P3, as illustrated in FIG. 7.

For the embodiments shown in FIGS. 6, 7, and 9, the power of the outer zone 315 decreases from some predetermined power at the radius $r_{in}$ or $r_{tran}$ to a power at the outer radius $r_{out}$ that is less than the paraxial power P1. Alternatively, the variation of power with radius over the outer zone 315 decreases to a power at the outer radius $r_{out}$ that is greater than or equal to the paraxial power P1.

The zones 314, 315 may be configured such that the optic 311 has a variation in optical power over the entire clear aperture that is less than or equal to 1.5 Diopters or less than or equal to 1 Diopter. The total variation in optical power over the entire clear aperture may be selected in accordance with specific design parameters such as the range of pseudo-accommodation to be provided, the required visual acuity at one or more specific object distance, the zone diameters, the pupil size under certain lighting conditions, the expected variation in pupil size, a desired mixture of near, intermediate, and/or distant vision for one or more pupil sizes, and the like.

The optic 311 illustrated in FIG. 5 is circular; however, other shapes may be used, for example, to enhance the insertion characteristics of the intraocular lens 310 into the eye 90 through a small incision. Also, at least one of the zones 314, 315 may comprise a cylinder power, for example, to correct for an astigmatism of the eye 90. While not illustrated in the FIG. 4 or 5, it will be appreciated that the intraocular lens 310 may generally comprise other features and elements such as edge features for reducing glare and/or reducing PCO, haptics for centering the intraocular lens 310 within the eye 90, and/or a positioning structure for providing accommodative axial motion and/or deformation of the optic 311. The optic 311 may be a single optic or part of a lens system, for example, one of the lenses of a two lens accommodating intraocular lens. In addition, the intraocular lens 310 may be configured to attenuate light over a band of wavelengths light outside a band of wavelengths. In such embodiments the intraocular lens 310 or the optic 311 may incorporate one or more dyes or other substances or devices for selectively blocking incident radiation, for example, to selectively blocking UV radiation or light in the violet or blue bands of the visible spectrum.

The intraocular lenses 310 may be fabricated with optical powers that vary from about 10 Diopters to about 30 Diopters in increments of about 0.5 Diopters. In some embodiments, intraocular lenses 310 may be produced that vary from about zero Diopters to about 40 Diopters or more. Alternatively or additionally, intraocular lenses 310 may be produced that have a negative optical power, for example that is within a range of less than about zero Diopters to greater than about −20 Diopters or less.

The intraocular lens 310 may generally be constructed of any of the various types of material known in the art. For example, the intraocular lens 310 may be a foldable lens made of at least one of the materials commonly used for resiliently deformable or foldable optics, such as silicone polymeric materials, acrylic polymeric materials, hydrogel-forming polymeric materials (e.g., polyhydroxyethylmethacrylate, polyphosphazenes, polyurethanes, and mixtures thereof), and the like. Other advanced formulations of silicone, acrylic, or mixtures thereof are also anticipated. Selection parameters for suitable lens materials are well known to those of skill in the art. See, for example, David J. Apple, et al., Intraocular Lenses: Evolution, Design, Complications, and Pathology, (1989) William & Wilkins, which is herein incorporated by reference. The lens material may be selected to have a relatively high refractive index, and thus provide a relatively thin optic, for example, having a center thickness in the range of about 150 microns to about 1000 microns, depending on the material and the optical power of the lens. At least portions of the intraocular lens 310, for example one or more haptics or fixation members thereof, may be constructed of a more rigid material including such polymeric materials as polypropylene, polymethylmethacrylate PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In some embodiments, the optic and haptic portions of the intraocular lens 310 are integrally formed of a single common material.

In certain embodiment, for example as illustrated in FIG. 4, a pair of rays 302a, 302b from the light 102 impinge upon the outer zone 315 near the outer periphery thereof and near the central zone 314, respectively. At least one of the surfaces 312, 313 in the region of the outer zone 315 is preferably aspheric in shape, such that light passing through the outer zone 315 is focused to substantially a single point or focus (e.g., to within a circle about the size of an Airy disk defining a diffraction limit of the zone 315). For example, the outer zone 315 may be configured to have at least some of the features and/or functions describe above with regards to the optic 211 illustrated in FIG. 3. In this regard, the outer zone 315 may comprise a monochromatic aberration, such as a spherical aberration, that corrects or at least partially compensates for an aberration of the eye (e.g., a spherical aberration introduced by the cornea 108). Additionally or alternatively, the outer zone 315 may incorporate a chromatic aberration, for example, through the use of a diffractive grating or phase plate on one of the lens surfaces. The aberration of the outer zone 315 may be selected to correct the aberrations of an individual cornea, in which case the intraocular lens 310 may be a custom intraocular lens. Alternatively, the intraocular lens 310 may be selected from a plurality intraocular lenses or optic portions having the same optical power, but differing amounts of spherical aberration. Alternatively, the aberration of the outer zone 315 may be selected to compensate for an aberration of a cornea that is part of an eye model and/or that represents an average cornea based on a particular population (e.g., an average spherical aberration for a population of people of a particular age group or that are likely candidates of a particular surgical procedure). At least one of the surfaces 312, 313 within the outer zone 315 of the intraocular lens 310 may be characterized by an equation defining a conoid of rotation, wherein a surface sag profile varies according to the relation:

$$\frac{cr^2}{1+\sqrt{1-(1+k)c^2r^2}}$$

where c is a base curvature of the surface portion (which is equal to 1/R, where R is the radius of curvature, k is a conic constant, and r is the radial distance from the optical axis OA. Depending on the value of k the first term is a conic section and describes a:

| | |
|---|---|
| hyperbola | $k < -1$ |
| parabola | $k = -1$ |
| prolate ellipse | $-1 < k < 0$ |
| circle | $k = 0$ |
| oblate ellipse | $k > 0$ |

Alternatively, at least one of the surfaces 312, 313 within the outer zone 315 of the intraocular lens 310 may be characterized by an equation defining a modified conoid of rotation, wherein a surface sag profile varies according to the relation:

$$\frac{cr^2}{1+\sqrt{1-(1+k)c^2r^2}} + a_4r^4 + a_6r^6 + \dots$$

where $a_2, a_4, \dots$ are constants, c is a base curvature of the surface portion (which is equal to 1/R, where R is the radius of curvature, k is a conic constant, and r is the radial distance from the optical axis OA. In certain embodiments, other portions of at least one of the surfaces 312, 313 outside the outer zone 315 (e.g., the central zone 314) may be characterized by the equation defining a conoid of rotation or by the equation defining a modified conoid of rotation, where the constant value may be different that those describing the surface 312, 313 within the outer zone 315.

It will be appreciated that the local radius of curvature of the anterior and posterior surfaces 312, 313, or some portion thereof, may be at least approximately related to a local power D at a given radius r (e.g., a power from FIG. 6) of the optic 311 by the equations:

$$D(r) = (n_l - n_o)\left(\frac{1}{R_1} - \frac{1}{R_2}\right) + b_1r^2 + b_2r^2 + \text{higher order terms of } r^2,$$

where $n_l$ is equal to the refractive index of the optic 311 material, $n_o$ is equal to the refractive index of the medium in which the optic 311 is place (e.g., typically 1.336 in an eye), $R_1$ is the local radius of curvature of the anterior surface 312, $R_2$ is the local radius of curvature of the posterior surface 313, and $b_1$ and $b_2$ are constants for the anterior and posterior surfaces 312, 313, respectively. When one or both surfaces are described by a conoid of rotation, $b_1$ and $b_2$ may be set equal to $2(1+k_1)(1/R_1)^3$ and $2(1+k_2)(1/R_2)^3$, respectively, where $R_1$ and $R_2$ are radius of curvatures at radius r on the surfaces 312 and 313, respectively, and $k_1$ and $k_2$ are conic constants at radius r on the surfaces 312 and 313, respectively.

Figure 10:
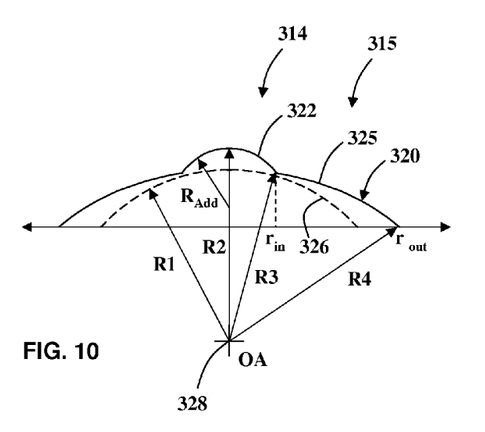
FIG. 10 is a cross-sectional profile of an optical surface of the intraocular lens shown in FIGS. 4 and 5 according to an embodiment of the present invention.

Referring to FIG. 10, a cross-sectional profile 320 of the anterior surface 312 is illustrated along a plane that is parallel to, and passes through, the optical axis OA. For clarity, the profile of the posterior surface 313 is not shown. In certain embodiments, the posterior surface 313 is a spherical surface having a constant radius of curvature. Alternatively, the posterior surface 313 has an aspheric profile that is configured to have or produce either no spherical aberration or a negative spherical aberration configured to help reduce or eliminate a positive spherical aberration of the optic 311 and/or the cornea 108.

The profile 320 has a central profile 322 that has a radius of curvature $R_{Add}$ along the central portion 314 of the optic 311. The radius of curvature $R_{Add}$ is configured to have a power to provide intermediate vision or a best visual acuity or best MTF for objects located at a hyperfocal distance (e.g., at 2.5 meters or at about 2.5 meters from the eye 90).

The profile 320 also includes an outer aspheric profile 325 along the outer portion 315. The aspheric profile 325 has a base curve 326 (shown by a dashed line in FIG. 10) with a radius of curvature R1 and a center of curvature 328 located along the optical axis OA. The aspheric profile 325 is configured to provide emmetropia or distant vision when the optic 311 is disposed within the eye 90. The aspheric profile 325 may be configured as a conoid of rotation having a conic constant that is −1 or about −1 (wherein the aspheric profile 325 has no or little spherical aberration), or less than −1 (wherein the aspheric profile 325 has a negative spherical aberration, for example to reduce or eliminate a positive spherical aberration of the opposite surface 313 and/or a positive spherical aberration of the cornea 108).

At the optical axis OA, the profile 320 has a radius of R2 from the center of curvature 328 that is generally greater than the radius R1. At radius $r_{in}$ from the optical axis OA, the profile 320 has a radius of R3 from the center of curvature 328, while at outer radius $r_{out}$ from the optical axis OA, the profile 320 has a radius of R4 from the center of curvature 328.

Figure 11:
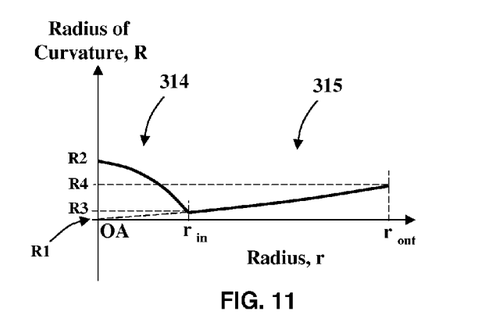
FIG. 11 is a plot of the cross-sectional profile of an optical surface of the intraocular lens shown in FIGS. 4 and 5 according to an embodiment of the present invention.

Referring to FIG. 11, the profile 320 may be plotted in terms of distance from the center of curvature 328 of the base curve 326 as a function of radius r from the optical axis OA. As illustrated, the central zone 314 has a radius from the center of curvature 328 that decreases from the optical axis OA to radius $r_{in}$, while the outer zone 315 has a radius R3 that is greater than R1 of the base curve 326 and increase to radius R4 at $r_{out}$. The increasing radius of the outer zone 315 may be configured to reduce or eliminate a positive spherical aberration of a wavefront that is incident upon the optic 311 and outer zone 315.

Figure 12:
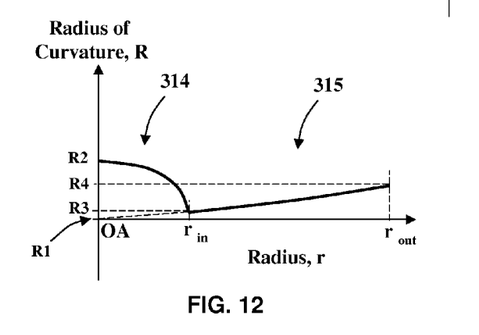
FIG. 12 is a plot of the cross-sectional profile of an optical surface of the intraocular lens shown in FIGS. 4 and 5 according to another embodiment of the present invention.

Referring to FIG. 12, the central portion 314 and the central profile 322 may be configure to deviate from a spherical shape, for example, to provide an extended depth of focus. The deviation from a spherical shape may be noted in the plot shown in FIG. 12 by the sharp slope near $r_{in}$.

In certain embodiments, the profiles shown in FIG. 11 or 12 may be applied to the posterior surface 313, wherein the anterior surface 312 may be spherical or some other shape. In other embodiments, the profile shown in FIG. 12 for the central zone 314 is applied to one of the surfaces 312, 313, while the profile shown in FIG. 12 for the outer zone 315 is applied to the opposite surface of the optic 311.

Figure 13:
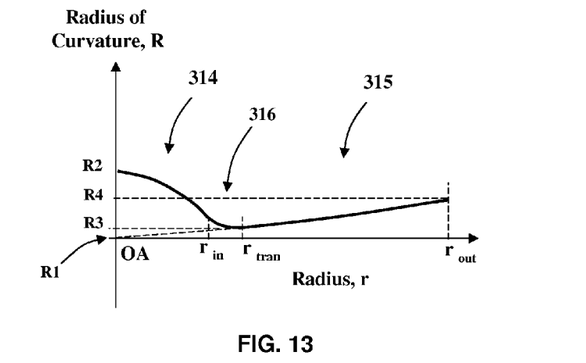
FIG. 13 is a plot of the radius of curvature profile of a surface of the intraocular lens shown in FIGS. 4 and 5 according to yet another embodiment of the present invention.

Referring to FIG. 13, the profile 320 may include a transition zone 316, for example, to smoothly blend the central profile 322 and the outer aspheric profile 325.

The performance of the optic 311 will now be described in terms of ray tracing characteristics. The aberration of the outer zone 315 may be selected to completely or substantially completely compensate for a spherical aberration of a cornea or eye. Alternatively, the aberration of the outer zone 315 may be selected to only partially compensate for (or over compensate for) the spherical aberration or other aberration of the cornea or eye. In this regard, it may be advantageous in certain embodiments to select the aberration of the outer zone 315 to leave a residual aberration when combined with a cornea, for example, as discussed in U.S. Pat. No. 7,350,916, which is herein incorporated by reference in its entirety. For instance, the intraocular lens 310 may comprise an outer zone 315 that has an optical power that is about 20 Diopters and a negative spherical aberration that partially correct a positive spherical aberration of the cornea, wherein the outer zone 315 has a negative spherical aberration that is between about −0.19 and about −0.202 microns, or that is about −0.156 microns. The eye may have a residual aberration that is essentially zero or is greater than zero (e.g., a residual aberration of about +0.14 microns or between about +0.006 microns and about +0.090 microns has been reported as potentially beneficial, for example, when placed in an eye or an eye model with a corneal spherical aberration of about 0.327 microns). In other embodiments, the intraocular lens 310 is configured with an outer zone 315 in which the optical power at the periphery of the zone is about 0.5 to about 0.75 Diopters less than the optical power at or near the boarder between the zones 314, 315.

As discussed above, the central zone 314 has an optical power that ranges from P1 at or near the center to P2 at or near the periphery of the zone, while the outer zone 315 has a power P3. In certain embodiments, the first optical power P1 and/or the third optical power P3 is less than the second optical power P2 by an amount that is less than or equal to about 1.5 or 2 Diopters, preferably less than or equal to about 1.0 Diopter, and in some cases less than or equal to about 0.5 Diopters. In some embodiments, the variation in optical power over the entire clear aperture (e.g., within and between the zones 314, 315) is less than or equal to about 0.5 Diopter plus the variation in optical power produces by the spherical aberrations of a spherical optic having a nominal optical power equal to that of the third optical power P3.

In the illustrated embodiment, the difference between the second optical power P2 of the central zone 314 and the first and/or third optical powers P1, P3 represents an add power AD, where the add power AD is generally smaller than the add power of a typical multifocal intraocular lens, which generally have add powers in the range of about 2 Diopters to about 4 Diopters (see, for example, U.S. Pat. Nod. 6,527,389, 5,225,858, and 6,557,992, which are herein incorporated by reference in their entirety. As used herein, the term "add power" means a change in optical power from an optical power necessary to provide distance vision. As used herein, the "add power" is the change in power at the principal plane of the intraocular lens (e.g., an intraocular lens add power of 4.0 Diopters is approximately equal to an increase in optical power of about 3.2 Diopters in the spectacle lens). Surprisingly, the use of a relatively small add power according to embodiments of the invention (e.g., of about one Diopter to about two Diopters) may beneficially provide better intermediate vision and/or near vision than if a larger add power were to be used in the central zone 314 (e.g., an add power of about 3 or 4 Diopters). This improved performance may, for example, be due to relatively low noise from halo effects when using a lower add power of about 1.0 to about 2.0 Diopters.

Embodiments of the intraocular lens 310 may be configured to provide a pupil 101 dependent visual acuity performance that is preferred over either a spherical intraocular lens such as the intraocular lens 110 or an aspheric intraocular lens such as the intraocular lens 210. For example, both zones 314, 315 in the illustrated embodiment focus light onto or near the retina 104 when the pupil 101 is relatively large, for instance under low lighting conditions or night time driving conditions. Because at least one of the surfaces 312, 313 in the vicinity of the outer zone 315 is aspheric, most of the light from distant objects entering the optic 311 is advantageously focused to substantially a single focus or point. This may provide better visual acuity than is generally possible with an optic having only spherical surfaces (e.g., the intraocular lens 110 illustrated in FIG. 1). The relative areas of the zones 314, 315 may be selected to provide more light energy for distant vision under lower lighting conditions. Thus, while some light from distant object entering the central zone 314 may be slightly defocused, relatively high visual acuity may be maintained, since most of the light entering the optic 311 under these conditions is focused by the outer zone 315 onto the surface of the retina 104

The intraocular lens 310 is also able to provide a pseudo-accommodative benefits under bright or intermediate lighting conditions in which the pupil 101 is small, since under these conditions all or most of the light entering the intraocular lens 310 passes through the central zone 314. Thus, the intraocular lens 310 is able to advantageously provide pseudo-accommodative benefits without significantly compromising the advantages of an aspheric intraocular lens over a spherical intraocular lens during night driving conditions.

The performance of the intraocular lens 310 under differing pupil sizes may be controlled by selecting the diameter of the central zone 314. For example, the central zone 314 may be configured to have an outer diameter D that is about the size of a typical pupil that is fully contracted, such as under sunny outdoor lighting conditions (e.g., the outer diameter D of the central zone 314 may about 1 millimeter, about 2 millimeters, or about 3 millimeters, or between about 2 millimeters and about 3 millimeters, depending on the relative performance desired between near, intermediate, and distant vision). In other embodiments, the diameter D is selected to provide predetermined areas ratios of the central and outer zones 314, 315 under specific lighting conditions or pupil sizes. Thus, the diameter D may be selected to provide a predetermined performance balance of distant visual acuity and enhanced DOF (or pseudo-accommodation) as a function of pupil size.

Figure 14:
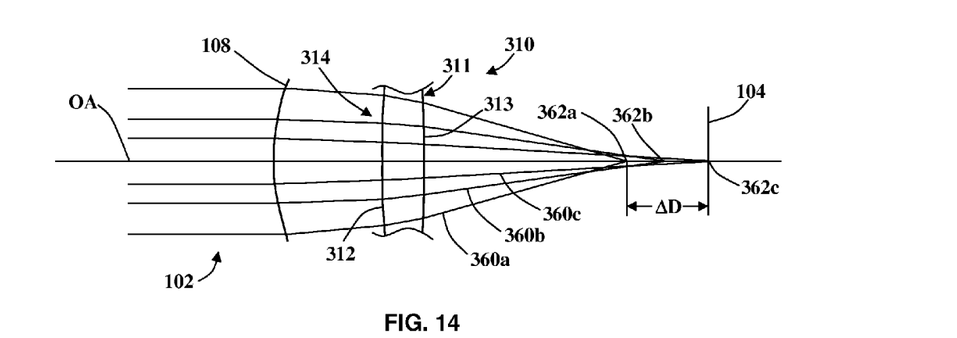
FIG. 14 is a magnified side view of the intraocular lens of FIG. 4 particularly showing the central zone of the intraocular lens according to an embodiment of the present invention.

To illustrate one way of configuring the central zone 314 to provide pseudo-accommodation, reference is now made to FIG. 14, which is a magnified side view of the central zone 314 of the optic 311. Three rays 360a, 360b, 360c are shown intercepting the central zone 314 at different radial distances from the optical axis OA. the peripheral ray 360a intercepts a peripheral region of the central zone 314 and is focused along the optical axis OA to a focus 362a, while the paraxial ray 360c intercepts the central zone 314 at or near the optical axis OA and is focused along the optical axis OA to a focus 362c. The intermediate ray 360b intercepts the central zone 314 at a location between the rays 360a, 360c and is focused along the optical axis OA to a focus 362c. In this case the peripheral ray 360a represents a maximum optical power (the first optical power P1) of the central zone 314. The focal length (or optical power) of the central zone 314 may be represented by the distance between the focal point 362b of the intermediate ray 360b and a principle plane of the central zone 314 or the optic 311. Alternatively, the focal length of the central zone 314 may be represented by another point between the foci 362a, 362c.

As illustrated in FIG. 14, the central zone 314 may comprise plurality of optical powers that progressively and continuously increases from the first optical power P1 (e.g., represented by the focus 362c) to the second optical power P2 (e.g., represented by the focus 362a) as the radius from the optical axis OA increases. In such embodiments, the third optical power P3 of the outer zone 315 may be selected to be equal that of first optical power P1 of the central zone 314 (e.g., as illustrated in FIG. 9). Alternatively, the variation in optical power of the central zone 314 with increasing radius from the optical axis OA may have discontinuities and/or may vary in a manner that is not progressive, depending on the particular design requirements or preferences of a designer, practitioner, and/or patient. As discussed in greater detail below, the central zone 314 may alternatively comprise plurality of optical powers that progressively and continuously decreases from a first optical power P1 (e.g., represented by the focus 362c' in FIG. 15) to the second optical power P2 (e.g., represented by the focus 362a' in FIG. 15) as the radius from the optical axis OA increases. In any event, the optic 311 is generally configured to provided enhanced visual acuity (e.g., with the outer zone 315) for distant vision and at least reasonably good visual acuity at intermediate distances under certain conditions (e.g., with the central zone 313). In one embodiment, the third optical power P3 is selected to provide distant vision when the intraocular lens is disposed within the eye, while the first and second optical powers P1, P2 are selected so that the central zone 314 provides a visual acuity of at least 20/30, or even 20/20, for objects located at a hyperfocal distance from the eye.

The paraxial ray 360c comes to focus on the retina 104 at the focus 362c, so that objects optical infinity are just focused and, therefore, at least somewhat resolved by the eye 90. Referring to the discussion above with regards to FIG. 2, the central zone 314 may be similarly constructed to the optic 211 (e.g., comprising anterior and posterior surfaces that are spherical) so that objects located at the hyperfocal distance advantageously cause the peripheral ray 360a to be focused on the retina 104 and, therefore, to provide a visual acuity of least 20/40, 20/30, or even 20/20. Thus, the central zone 314 in the illustrated embodiment has an extended DOF (represented by the distance ΔD) that provides pseudo-accommodation, by allowing objects located at distances between optical infinity and the hyperfocal distance to resolved by the eye 90. For object closer than the hyperfocal distance, all the light or rays are generally focused posteriorly to the retina 104, wherein other devices or means may be necessary to provide a desirable level of visual acuity.

In some embodiments, at least one of the surfaces of the central zone 314 has a positive spherical aberration that is greater than or less than that of an equivalent spherical surface having substantially the same focal length or optical power. In general the amount of positive spherical aberration may be selected to provide a predetermined DOF and/or add power, as represented by ΔD in FIG. 14. For example, at least one of the surfaces 312, 313 in the vicinity of the central zone 314 may an oblate surface that has a greater curvature in the periphery than in the center. In such embodiments, the central zone 314 may be configured to suitably resolve objects that are closer than the hyperfocal distance and/or provide enhanced intermediate vision.

Figure 15:
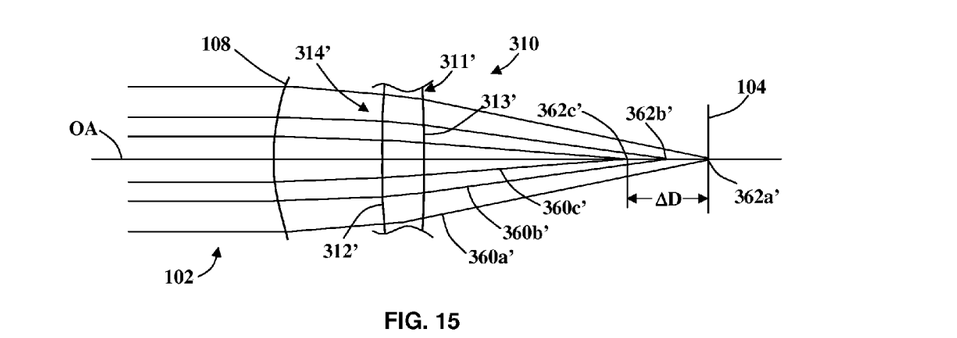
FIG. 15 is a magnified side view of the intraocular lens of FIG. 4 particularly showing the central zone of the intraocular lens according to another embodiment of the present invention.

Referring to FIG. 15, the optic 311 may comprise a central zone 314' that has a negative spherical aberration. For example, in the illustrated embodiment, at least one of the surface 312', 313' has a negative spherical aberration that may be selected to produce an overall negative spherical aberration when placed in the eye of a subject. In effect, the optical power of central zone 314' generally decreases with increasing radial distance from the optical axis OA and may be configured such that the third optical power P3 of the outer zone 315 is equal or substantially equal that of the optical power P2 of the central zone 314. Thus, a peripheral ray 360a' of the central zone 314' is focused at or near the retina 104, while intermediate and paraxial rays 360b', 360c' are focused progressively closer to the central zone 314'. The resulting add power ΔD may be represented by the change in focal length over the central zone 314' (e.g., between the foci 362a' and 362c').

In certain embodiments, a method of making an intraocular lens comprises forming an anterior surface and an opposing posterior surface, the surfaces being disposed about an optical axis to provide a clear aperture. The method further comprises forming a central zone comprising a plurality of optical powers that progressively vary between a first optical power at a center of the central zone and a second optical power at a periphery of the central zone, the absolute value of the difference between the first optical power and the second optical power being between about 0.25 Diopter and about 1 Diopter. The method also comprises forming outer zone disposed about the central zone, the outer zone comprising a third optical power and an optional negative spherical aberration. The optic resulting from the method has a variation in optical power over the entire clear aperture that is less than about 1 Diopter.

While embodiments of the invention have been disclosed for an IOL suitable providing enhanced performance under non-optimal conditions, such as when the IOL is decentered from the optical axis of the eye, those skilled in the art will appreciate that embodiments of the invention are suitable for other ocular devices such as contact lenses and corneal implants. For instance, the method of designing a multi-zonal monofocal IOL may be adapted for improving the performance of contact lenses, which are known to move to different positions during use relative to the optical axis of the eye.

What is claimed is:

1. An intraocular lens, comprising:
an optic having a clear aperture having an outer diameter, the optic comprising:
a first surface and an opposing second surface, the surfaces being disposed about an optical axis, the first surface having a first radius of curvature at the optical axis and the second surface having a second radius of curvature at the optical axis;
a central zone disposed about the optical axis having an outer diameter sized such that under bright or intermediate lighting conditions most of the light passing through the pupil and entering the IOL passes through the central zone and wherein the central zone has an optical power that progressively and continuously increases from a first paraxial optical power at the optical axis selected to provide hyperfocal vision when the intraocular lens is disposed within an eye to a second optical power at the outer diameter that is greater than the first paraxial optical power, wherein the difference in the optical power between the first paraxial optical power and the second optical power is less than or equal to about 1.5 diopters and the second optical power is greater than or equal to the optical power of a reference spherical lens at a diameter equal to the outer diameter of the central zone, the reference spherical lens having a paraxial optical power equal to the first paraxial optical power, a first surface radius of curvature equal to the first radius of curvature at the optical axis, and a second surface radius of curvature equal to the second radius of curvature at the optical axis; and
an outer zone disposed about the central zone, the outer zone comprising an inner diameter and an outer diameter equal to the outer diameter of the clear aperture, the outer zone characterized by a third optical power at the inner diameter which is less than the first paraxial optical power and selected to provide distance vision when the intraocular lens is disposed within the eye, wherein the outer zone further comprises a negative spherical aberration,
wherein the central zone and the outer zone are the only two zones in the optic and entirely fill the clear aperture of the optic, wherein the variation in optical power over the entire clear aperture is less than or equal to 2.0 diopters,
and wherein the central and outer zones are configured such that more light for distant vision under low lighting conditions is focused by the outer zone onto the surface of the retina.

2. The intraocular lens of claim 1, wherein the difference between the third optical power and the first optical power is about 0.4 Diopter.

3. The intraocular lens of claim 1, wherein the absolute value of the difference between the first optical power and the second optical power is about one Diopter.

4. The intraocular lens of claim 1, wherein the optic has a variation in optical power over the clear aperture that is less than about 1.5 Diopters.

5. The intraocular lens of claim 1, wherein the variation in optical power over the clear aperture is less than or equal to about 0.5 Diopter plus the variation in optical power produced by the spherical aberrations of a spherical optic having a nominal optical power that is equal to the third optical power of the outer zone.

6. The intraocular lens of claim 1, wherein the first and second surfaces in the vicinity of the central zone comprises spherical surfaces.

7. The intraocular lens of claim 1, wherein the first zone and the second zone have at least one surface with a cross-sectional profile described by a polynomial and/or spline.

8. The intraocular lens of claim 1, wherein at least one of the zones has a cylinder power.

* * * * *